(12) United States Patent
Masuda

(10) Patent No.: US 9,931,080 B2
(45) Date of Patent: Apr. 3, 2018

(54) CATHETER

(71) Applicant: Japan Lifeline Co., Ltd., Tokyo (JP)

(72) Inventor: Takuya Masuda, Tokyo (JP)

(73) Assignee: Japan Lifeline Co., Ltd., Tokyo (JP)

( * ) Notice: Subject to any disclaimer, the term of this patent is extended or adjusted under 35 U.S.C. 154(b) by 0 days.

(21) Appl. No.: 15/659,166

(22) Filed: Jul. 25, 2017

(65) Prior Publication Data

US 2017/0319138 A1    Nov. 9, 2017

Related U.S. Application Data

(63) Continuation of application No. PCT/JP2016/070909, filed on Jul. 14, 2016.

(30) Foreign Application Priority Data

Jan. 29, 2016 (JP) .................................. 2016-015336

(51) Int. Cl.
*A61B 5/00* (2006.01)
*A61B 5/01* (2006.01)

(52) U.S. Cl.
CPC .............. *A61B 5/6852* (2013.01); *A61B 5/01* (2013.01); *A61B 5/687* (2013.01); *A61B 2560/0431* (2013.01)

(58) Field of Classification Search
CPC ............................... A61B 5/6852; A61B 5/687
See application file for complete search history.

(56) References Cited

U.S. PATENT DOCUMENTS

| 2008/0177175 A1 | 7/2008 | Mottola et al. |
| 2012/0035603 A1 | 2/2012 | Lenihan |
| 2012/0209122 A1 | 8/2012 | Garbini et al. |
| 2014/0180252 A1 | 6/2014 | Gabriel |

FOREIGN PATENT DOCUMENTS

| JP | 2010-505592 A | 2/2010 |
| JP | 2012-515612 A | 7/2012 |
| JP | 2012-166032 A | 9/2012 |
| JP | 2014-128653 A | 7/2014 |
| JP | 2015-173681 A | 10/2015 |
| WO | WO 2008-045869 A2 | 4/2008 |
| WO | WO 2010-090701 A1 | 8/2010 |

OTHER PUBLICATIONS

International Search Report for International Application No. PCT/JP2016/070909, dated Oct. 18, 2016.

*Primary Examiner* — Michael C Stout
*Assistant Examiner* — Nicholas E Kolderman
(74) *Attorney, Agent, or Firm* — Wolf, Greenfield & Sacks, P.C.

(57) ABSTRACT

Provided is a catheter that includes a catheter tube and a temperature sensor. The catheter tube includes a tip-flexible part and a base end part. The base end part includes a first base end section having rigidity higher than the tip-flexible part, and a second base end section having rigidity lower than the first base end section. The tip-flexible part has an axial length from 40 mm to 100 mm, the first base end section has an axial length from 200 mm to 400 mm, and the second base end section has an axial length from 200 mm to 900 mm. A value of the rigidity of each of the first and the second base end sections decreases linearly from the first base end section to the second base end section, in a region around a boundary between the first base end section and the second base end section.

6 Claims, 4 Drawing Sheets

CATHETER

CROSS REFERENCE TO RELATED APPLICATIONS

This is a continuation of International Application No. PCT/JP2016/070909, filed Jul. 14, 2016, which claims the benefit of Japanese Priority Patent Application JP2016-015336, filed Jan. 29, 2016, the entire contents of both of which are incorporated herein by reference.

BACKGROUND

The technology relates to a catheter having a temperature sensor.

An operation that performs cauterization or "ablation" with use of an ablation catheter has been performed as one of medical treatments for arrhythmia, etc. Such ablation that uses the ablation catheter may be performed on a site that involves the arrhythmia inside the heart, for example. In general, methods of the ablation may be roughly classified into a method that performs heating and a method that performs cooling. More specifically, the methods of the ablation may be roughly classified into a high-temperature ablation that uses a high frequency current and a low-temperature ablation that uses liquid nitrous oxide, liquid nitrogen, etc. When performing the ablation of a site such as the posterior wall of the left atrium of the heart by means of the ablation catheter, i.e., upon surgical ablation of the left atrium, the esophagus located in the vicinity of the posterior wall of the left atrium may typically be heated or cooled as well, leading to a possible damage of the esophagus.

To address this, a method has been proposed that measures or monitors information on a temperature in the esophagus, such as a temperature of the medial wall of the esophagus. The method involves insertion of a temperature measuring catheter or a so-called "esophageal catheter" into the esophagus through the nose of a patient by means of a transnasal approach. For example, reference is made to Japanese Unexamined Patent Application Publication (Translation of PCT Application) No. 2010-505592 and Japanese Unexamined Patent Application Publication (Translation of PCT Application) No. 2012-515612. The temperature measuring catheter includes a temperature sensor in the vicinity of a metal ring located near a tip of a catheter tube. The temperature sensor measures a temperature in the esophagus. A system that achieves such a method, or a "catheter system", includes the foregoing temperature measuring catheter and a temperature measuring apparatus that measures the temperature in the esophagus by means of the temperature sensor of the temperature measuring catheter.

Monitoring the temperature in the esophagus in such a manner makes it possible to avoid the possible damage of the esophagus upon, for example, the foregoing surgical ablation of the left atrium.

SUMMARY

In general, it is required that a temperature measuring catheter be able to improve convenience upon use. What is therefore desired is a proposal of a method that makes it possible to improve the convenience.

It is desirable to provide a catheter that makes it possible to improve convenience upon use.

A catheter according to an embodiment of the technology measures an internal temperature of a hollow organ inside a body. The catheter includes: a catheter tube including a tip-flexible part and a base end part, in which the tip-flexible part is configured to perform a deflection operation, and the base end part is provided at a base end of the tip-flexible part; and one or a plurality of temperature sensors provided in the tip-flexible part. The base end part includes a first base end section and a second base end section. The first base end section is provided closer to the tip-flexible part than the second base end section, and has rigidity that is higher than rigidity of the tip-flexible part. The second base end section is provided at a base end of the first base end section, and has rigidity that is lower than the rigidity of the first base end section. The tip-flexible part has a length in an axial direction of the tip-flexible part in a range from 40 mm to 100 mm, the first base end section has a length in an axial direction of the first base end section in a range from 200 mm to 400 mm, the second base end section has a length in an axial direction of the second base end section in a range from 200 mm to 900 mm, and a value of the rigidity of the first base end section and a value of the rigidity of the second base end section decrease linearly from the first base end section to the second base end section, in a region around a boundary between the first base end section and the second base end section.

It is to be understood that both the foregoing general description and the following detailed description are exemplary, and are intended to provide further explanation of the technology as claimed.

BRIEF DESCRIPTION OF THE DRAWINGS

The accompanying drawings are included to provide a further understanding of the disclosure, and are incorporated in and constitute a part of this specification. The drawings illustrate embodiments and, together with the specification, serve to explain the principles of the technology.

DETAILED DESCRIPTION

Figure 1:
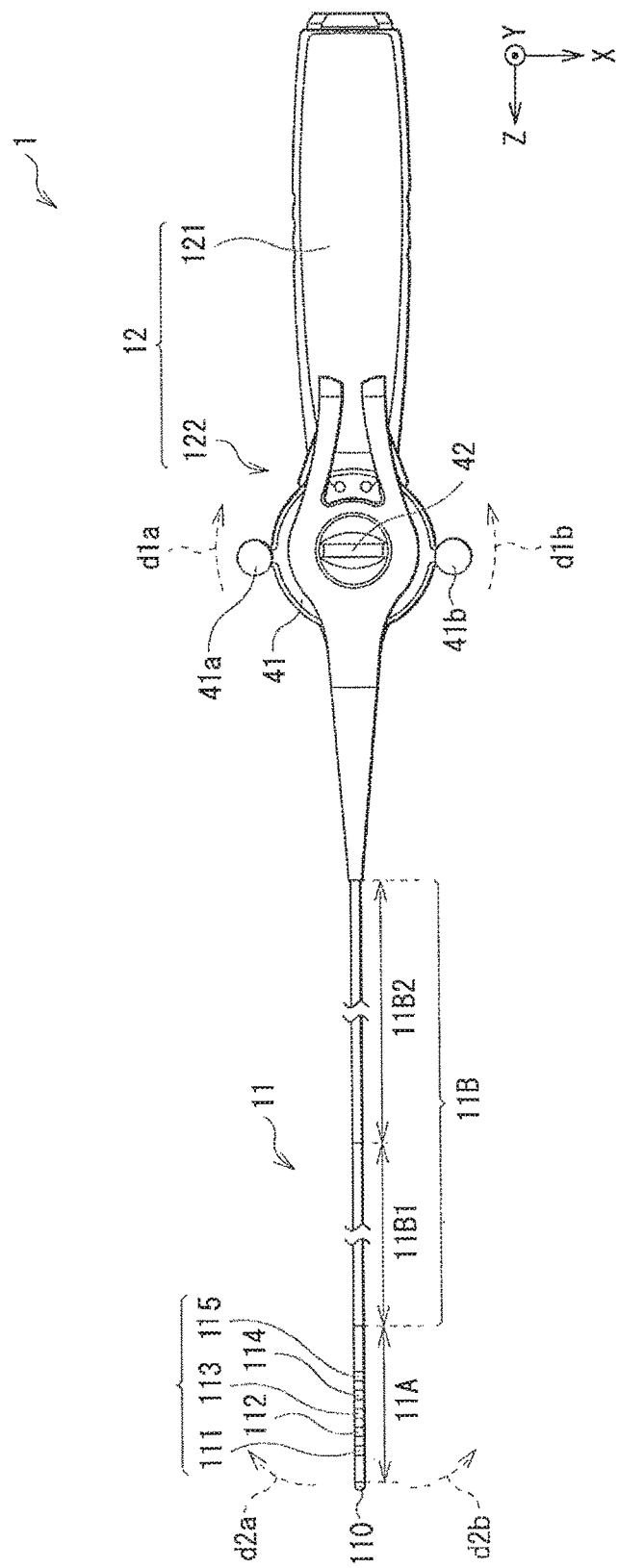
FIG. 1 schematically illustrates an example of an outline configuration of a catheter according to an embodiment of the technology.

Some example embodiments of the technology are described in detail below, in the following order, with reference to the drawings.

1. Example Embodiment (an example of a configuration of a catheter in which rigidity of a second base end section is lower than rigidity of a first base end section)
2. Modification Examples Note that the following description is directed to illustrative examples of the technology and not to be construed as limiting to the technology. Factors including, without limitation, numerical values, shapes, materials, components, positions of the components, and how the components are coupled to each other are illustrative only and not to be construed as limiting to the technology. Further, elements in the following example embodiments which are not recited in a most-generic independent claim of the technology are optional and may be provided on an as-needed basis. The drawings are schematic and are not intended to be drawn to scale. Note that the like elements are denoted with the same reference numerals, and any redundant description thereof will not be described in detail.

EXAMPLE EMBODIMENT

[Example of Outline Configuration]

FIG. 1 schematically illustrates an example of an outline configuration, on a Z-X plane, of a catheter referred to as a "catheter 1" according to an example embodiment of the technology. The catheter 1 may be a catheter or a so-called "esophageal catheter" used for measurement of information on an internal temperature of a hollow organ inside the body of a patient upon performing a medical treatment of, for example, arrhythmia of the patient, e.g., upon performing surgical ablation of the left atrium. For example, the hollow organ may be the digestive system such as the esophagus. The internal temperature may be a temperature of the medial wall of the hollow organ. More specifically, the catheter 1 may be inserted into the esophagus, or any other part, of the patient through the nose by means of a transnasal approach, as described later in greater detail.

Referring to FIG. 1, the catheter 1 includes a catheter tube 11 or a "catheter shaft", and a handle 12 attached at a base end of the catheter tube 11. The catheter tube 11 may serve as a catheter body or an "elongated part".

[Catheter Tube 11]

The catheter tube 11 may have a tubular structure having flexibility, and has a shape that extends in an axial direction thereof, i.e., in a Z-axis direction. In other words, the catheter tube 11 may be a hollow tube-shaped member. More specifically, a length in the axial direction of the catheter tube 11 may be about several times to about several ten times as long as a length in an axial direction, i.e., in the Z-axis direction, of the handle 12.

The catheter tube 11 has a tip end part and a base end part 11B as illustrated in FIG. 1. The tip end part, or a "tip-flexible part 11A", has a relatively superior flexibility, and is so configured as to perform a later-described deflection operation. The base end part 11B may be formed integrally with the tip-flexible part 11A in the axial direction, and has relatively higher rigidity than rigidity of the tip-flexible part 11A. The base end part 11B is disposed at a base end of the tip-flexible part 11A, and has a first base end section 11B1 and a second base end section 11B2 as illustrated in FIG. 1. The first base end section 11B1, or an "intermediate part", is disposed on the side on which the tip-flexible part 11A is located. In other words, the first base end section 11B1 is disposed closer to the tip-flexible part 11A than the second base end section 11B2. The second base end section 11B2, or a "rear end part", is disposed at a base end of the first base end section 11B1. Note that an example of a detailed configuration, such as an example of characteristics of rigidity, of each of the tip-flexible part 11A, the first base end section 11B1, and the second base end section 11B2 is described later in greater detail with reference to FIG. 3.

The catheter tube 11 may also have a so-called single lumen structure in which a single lumen is so formed therein as to extend in the axial direction thereof, or a so-called multi-lumen structure in which a plurality of lumens, such as four lumens, are formed therein. The term "lumen" as used herein may encompass an inner hole, a pore, or a through hole. Alternatively, the catheter tube 11 may include therein both a region having the single lumen structure and a region having the multi-lumen structure. Such a lumen provided in the catheter tube 11 may include various fine wires that are inserted therethrough while they are electrically insulated from one another. Examples of the various fine wires may include a pair of operating wires and conduction wires L1 to L5 both of which are to be described later in greater detail.

The pair of operating wires, or "tension wires", among the various fine wires each may extend through the inside of the catheter tube 11 to be led to the inside of the handle 12. The pair of operating wires may be used upon the deflection operation of the tip-flexible part 11A. In other words, the operating wires each may be used to deflect a region near a tip end of the catheter tube 11 as exemplified by arrows d2a and d2b of FIG. 1. The operating wires each may have a tip end fixed around a tip end inside the catheter tube 11 by means of, for example, an anchor and a solder. The operating wires each may also have a base end that extends from the inside of the catheter tube 11 to the inside of the handle 12 as described above and fixed by an unillustrated fastener inside the handle 12. The operating wires each may be made of stainless steel (SUS) or a super-elastic metal material such as nickel titanium (NiTi), and each may have a diameter in a range from about 100 μm to about 500 μm. In one embodiment, the operating wires each may have a diameter of 200 μm without limitation. However, it is not strictly necessary for each of the operating wires to be made of a metal material. For example, the operating wires each may be a high-strength non-conductive wire or other suitable wire.

The catheter tube 11 may be made of a synthetic resin such as polyolefin, polyamide, polyetherpolyamide, polyurethane, nylon, and polyether blockamide.

The length in the axial direction of the catheter tube 11 may preferably be in a range from about 500 mm to about 1200 mm, and may be 800 mm according to a preferred but non-limiting embodiment. The tip-flexible part 11A of the catheter tube 11 may have a length in the axial direction which may preferably be in a range from 40 mm to 100 mm, and more preferably be in a range from 50 mm to 80 mm. The base end part 11B may have a length in the axial direction which may preferably be in a range from 400 mm to 1100 mm, and more preferably be in a range from 600 mm to 900 mm. The first base end section 11B1 of the base end part 11B may have a length in the axial direction which may preferably be in a range from 200 mm to 400 mm, and more preferably be in a range from 250 mm to 350 mm. Further, the second base end section 11B2 of the base end part 11B may have a length in the axial direction which may preferably be in a range from 200 mm to 900 mm, and more preferably be in a range from 350 mm to 700 mm. An outer diameter, i.e., an outer diameter in X-Y cross section, of the catheter tube 11 may be in a range from 1.3 mm to 4.0 mm, and may be 2.4 mm according to a preferred but non-limiting embodiment.

Further, one or a plurality of metal rings, such as five metal rings 111 to 115 in this example embodiment, and one tip 110 may be disposed at a predetermined interval near the tip end (i.e., the tip-flexible part 11A) of the catheter tube 11 as illustrated in FIG. 1. More specifically, the metal rings 111 to 115 serving as temperature measuring metal rings each may be fixedly disposed at a mid-part of the tip-flexible part 11A, i.e., around a middle region of the tip-flexible part 11A, whereas the tip 110 may be fixedly disposed at a most distal end of the tip-flexible part 11A.

Figure 2:
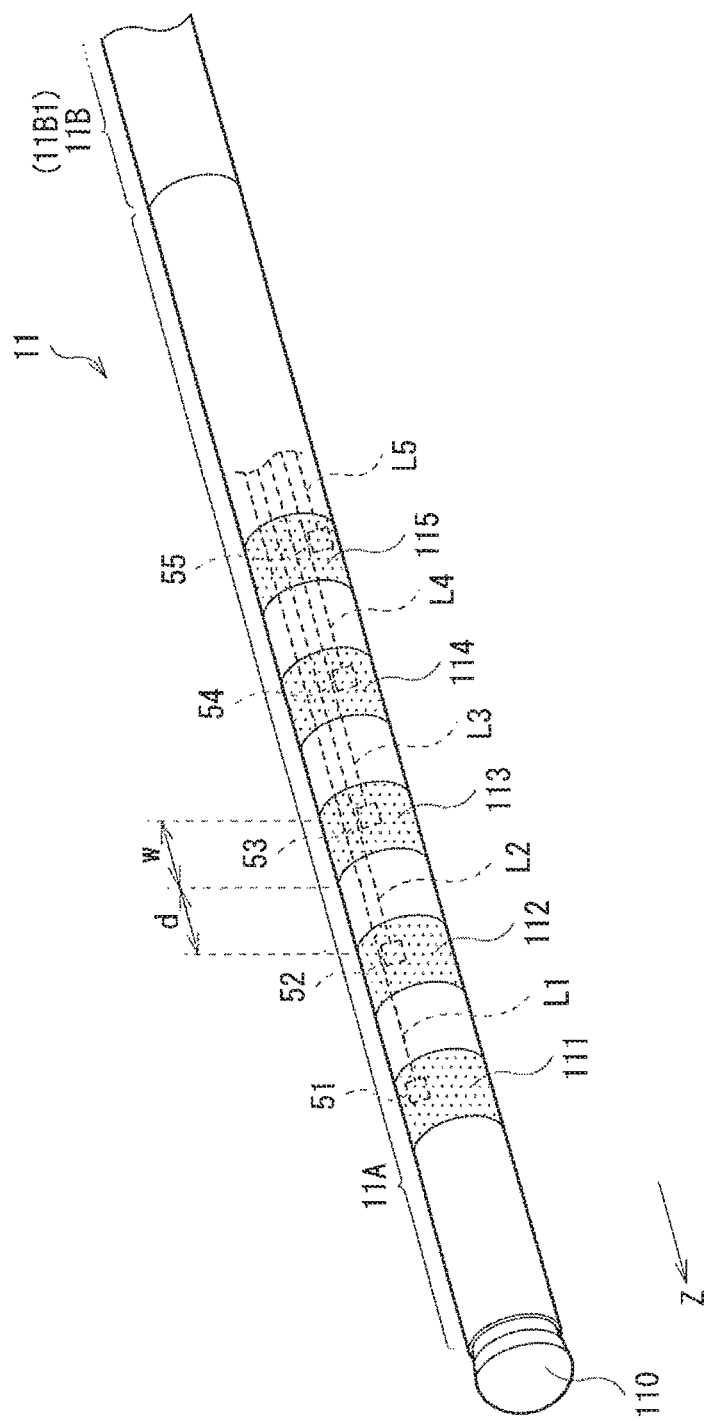
FIG. 2 schematically illustrates an example of a detailed configuration of a tip-flexible part of a catheter tube illustrated in FIG. 1.

FIG. 2 is a schematic perspective view of an example of a detailed configuration of a region near the tip end of the catheter tube 11, including the metal rings 111 to 115 and the tip 110. Referring to FIG. 2, the five metal rings 111 to 115 may be disposed side by side in this order at a predetermined interval from the tip end, i.e., from the tip 110, of the catheter tube 11 to a base end of the catheter tube 11. The predetermined interval is, in other words, a metal-ring-to-metal-ring distance "d" illustrated in FIG. 2. The metal-ring-to-metal-ring distance d may preferably be 10 mm or less, for example, and more preferably be in a range from about 2 mm to about 5 mm. According to one embodiment, the metal-ring-to-metal-ring distance d may be 5 mm without limitation. Further, the metal rings 111 to 115 each may have a metal ring width "w" illustrated in FIG. 2 which may preferably be 7 mm or less, for example, and more preferably be in a range from about one mm to about 5 mm. According to one embodiment, the metal ring width w may be 5 mm without limitation.

The metal rings 111 to 115 each may be made of a metal material having a favorable electrical conductivity, such as aluminum (Al), copper (Cu), stainless steel (SUS), gold (Au), and platinum (Pt). The tip 110 may also be made of a metal material similar to that of each of the metal rings 111 to 115, for example. Alternatively, the tip 110 may be made of a resin material such as a silicone rubber resin and polyurethane. An outer diameter of each of the metal rings 111 to 115 and the tip 110 is not particularly limited. According to one embodiment, without limitation, the metal rings 111 to 115 and the tip 110 each may preferably have the outer diameter that is about the same as the outer diameter of the catheter tube 11.

The tip-flexible part 11A of the catheter tube 11 is provided therein with five temperature sensors 51 to 55 that are respectively disposed near the metal rings 111 to 115 and disposed corresponding to the metal rings 111 to 115, respectively, as schematically illustrated in FIG. 2. For example, the temperature sensors 51 to 55 may be disposed at respective positions at which the temperature sensors 51 to 55 respectively face the metal rings 111 to 115. More specifically, in this example embodiment, a plurality of sets of metal rings 111 to 115 and temperature sensors 51 to 55, i.e., five sets configured by the five metal rings 111 to 115 and the five temperature sensors 51 to 55, are provided in a one-to-one correspondence relationship. Note that no temperature sensor that forms a pair with, or is electrically coupled to, the tip 110 may be provided near the tip 110 in this example embodiment.

The temperature sensors 51 to 55 each may serve as a sensor that measures the internal temperature of a site such as the esophagus upon, for example, the surgical ablation of the left atrium. The temperature sensors 51 to 55 may be electrically coupled to the metal rings 111 to 115 in an individual fashion, respectively. More specifically, the temperature sensor 51 may be embedded near the metal ring 111, and may be electrically coupled to the metal ring 111 as illustrated in FIG. 2. Similarly, the temperature sensor 52 may be embedded near the metal ring 112, and may be electrically coupled to the metal ring 112. The temperature sensor 53 may be embedded near the metal ring 113, and may be electrically coupled to the metal ring 113. The temperature sensor 54 may be embedded near the metal ring 114, and may be electrically coupled to the metal ring 114. The temperature sensor 55 may be embedded near the metal ring 115, and may be electrically coupled to the metal ring 115. For example, such electrical coupling may be achieved by an individual spot welding of the temperature sensors 51 to 55 onto corresponding inner circumferential surfaces of the respective metal rings 111 to 115.

The temperature sensors 51 to 55 each may have a configuration in which a thermocouple is used, for example. In other words, the temperature sensors 51 to 55 each may utilize a temperature measuring junction by means of the thermocouple. Further, the conduction wires L1 to L5 serving as leads may be electrically coupled to the temperature sensors 51 to 55 in an individual fashion, respectively, and may include metal wires. The metal wires are different in kind from each other and structure the thermocouple. The conduction wires L1 to L5 each may be inserted through the lumen provided in the catheter tube 11 and led to the inside of the handle 12 as described previously.

[Handle 12]

The handle 12 illustrated in FIG. 1 may be a part where an operator such as a doctor grabs or holds upon using the catheter 1. The handle 12 may have a handle body 121 and a rotary operation part 122 as illustrated in FIG. 1. The handle body 121 may be attached at the base end of the catheter tube 11. The rotary operation part 122 may correspond to an "operation part" in one specific but non-limiting embodiment of the technology.

The handle body 121 may be equivalent to a part or a "grip" where the operator actually holds, and may have a shape that extends in an axial direction, i.e., the Z-axis direction, of the handle body 121. The handle body 121 may be made of a synthetic resin such as polycarbonate and acrylonitrile butadiene styrene copolymer (ABS).

The rotary operation part 122 may be a part used upon performing the deflection operation, or a "deflection manipulation", that deflects the region near the tip end of the catheter tube 11 in conjunction with the previously-described pair of operating wires. The region near the tip end of the catheter tube 11 is, in other words, the tip-flexible part 11A. More specifically, the rotary operation part 122 is operated or subjected to a "rotary operation" upon performing such a deflection operation. This means that the rotary operation part 122 may serve as the operation part that allows the tip-flexible part 11A to perform the deflection operation. The rotary operation part 122 may include a rotary plate 41 and an adjustment knob 42 as illustrated in FIG. 1.

The rotary plate 41 may be a member rotatably attached to the handle body 121 around a rotation axis that is perpendicular to a longitudinal direction, i.e., the Z-axis direction, of the handle body 121. The rotation axis, in other words, corresponds to a Y-axis direction. The rotary plate 41 may be equivalent to a part actually operated by the operator upon the previously-described rotary operation, and may have a substantially disk-like shape. More specifically, in this example embodiment, an operation is made possible in which the rotary plate 41 is rotated in two ways in the Z-X plane relative to the handle body 121 as denoted by arrows d1a and d1b in FIG. 1. In other words, a rotary operation of the rotary plate 41 is made possible around the rotation axis.

The rotary plate 41 may be integrally provided with a pair of knobs 41a and 41b that are located on a side surface of the rotary plate 41. In this example embodiment, the knob 41a and the knob 41b may be disposed at their respective positions that are symmetric with respect to a point around the rotation axis of the rotary plate 41 as illustrated in FIG. 1. The knobs 41a and 41b each may be equivalent to a part operated or pushed by, for example, fingers of one hand when the operator performs the rotary operation of the rotary plate 41. For example, the rotary plate 41 may be made of a material similar to the previously-described material configuring the handle body 121, such as a synthetic resin.

The adjustment knob 42 may be a member that is rotatable in the Z-X plane, and fixes or keeps a position at which the rotary plate 41 is rotated. In other words, the adjustment knob 42 may fix or keep a state in which the region near the tip end of the catheter tube 11 is curved. More specifically, the operator may twist the adjustment knob 42 to fix the rotary plate 41 to the handle body 121. This allows for fixation of the position at which the rotary plate 41 is rotated.
[Example of Detailed Configuration of Catheter Tube 11]

Figure 3:
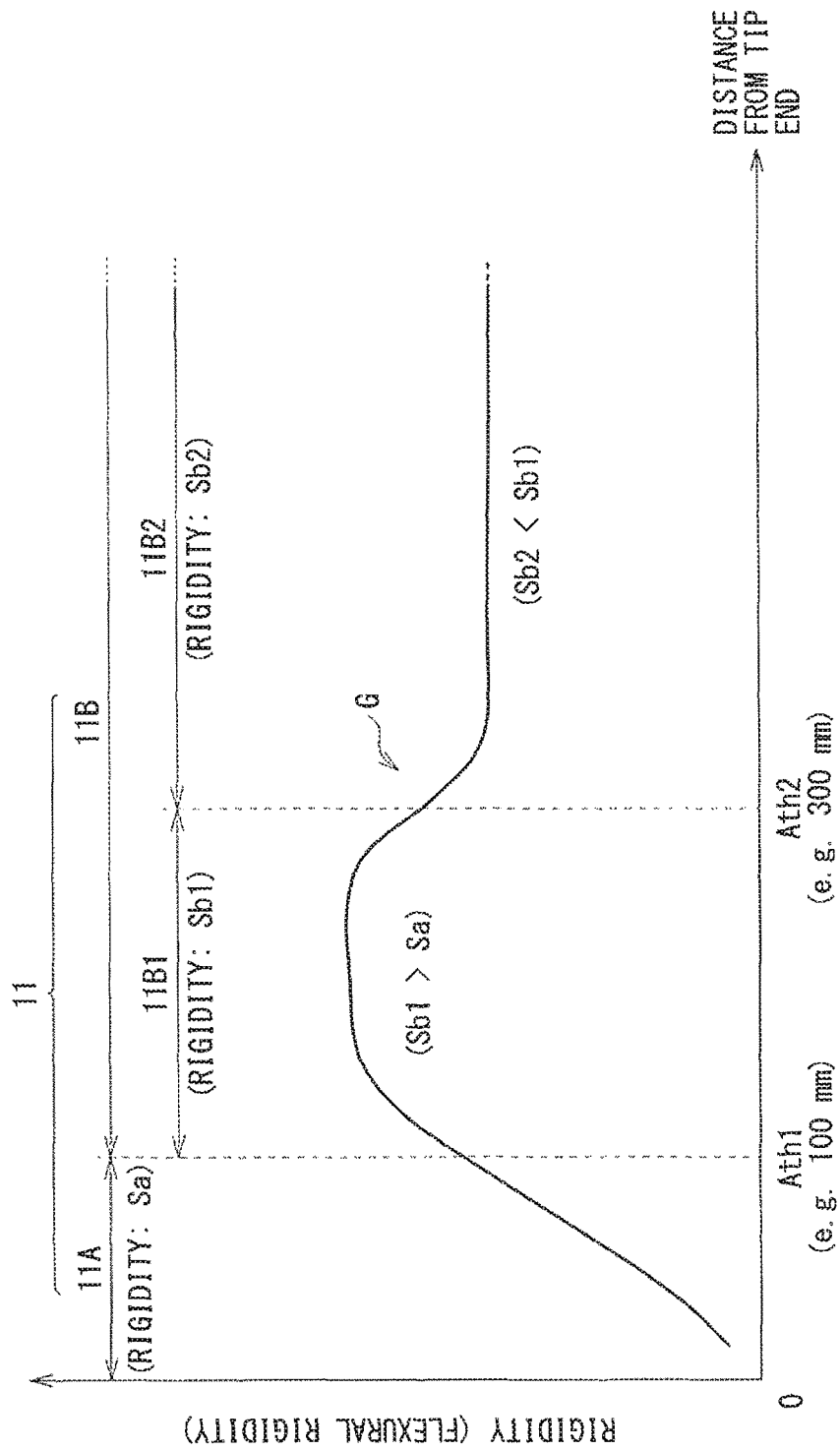
FIG. 3 schematically illustrates an example of characteristics of rigidity of the catheter tube illustrated in FIG. 1.

Referring to FIG. 3, description is given next of an example of the detailed configuration, including an example of the characteristics of the rigidity, of each of the tip-flexible part 11A, the first base end section 11B1, and the second base end section 11B2 of the catheter tube 11.

FIG. 3 schematically illustrates an example of the characteristics of the rigidity of the catheter tube 11. More specifically, FIG. 3 illustrates, for each of the tip-flexible part 11A, the first base end section 11B1, and the second base end section 11B2, an example of a relationship of a distance from the tip end of the catheter tube 11 versus the rigidity of the catheter tube 11. In other words, FIG. 3 illustrates an example of a relationship of a distance from a position located at a most distal end of the tip 110 versus flexural rigidity of the catheter tube 11, for each of the tip-flexible part 11A, the first base end section 11B1, and the second base end section 11B2.

A boundary Ath1 illustrated in FIG. 3 denotes a position of a boundary between the tip-flexible part 11A and the first base end section 11B1. According to one embodiment, a distance from the tip end to the boundary Ath1 may be 100 mm without limitation. A boundary Ath2 illustrated in FIG. 3 denotes a position of a boundary between the first base end section 11B1 and the second base end section 11B2. According to one embodiment, a distance from the tip end to the boundary Ath2 may be 300 mm without limitation.

Further, in the catheter tube 11, the second base end section 11B2 has rigidity Sb2 that is lower than rigidity Sb1 of the first base end section 11B1 (Sb2<Sb1) as denoted by a reference sign G of FIG. 3. According to one embodiment, a value of the rigidity Sb2 of the second base end section 11B2 may also be substantially flat, i.e., may be a substantially fixed value, in the axial direction of the catheter tube 11. The first base end section 11B1 has the rigidity Sb1 that is higher than rigidity Sa of the tip-flexible part 11A (Sb1>Sa). According to one embodiment, a value of the rigidity Sb1 of the first base end section 11B1 may also be substantially flat, i.e., may be a substantially fixed value, in the axial direction of the catheter tube 11 basically. Moreover, the value of the rigidity Sb1 of the first base end section 11B1 and the value of the rigidity Sb2 of the second base end section 11B2 each may gradually decrease from the first base end section 11B1 to the second base end section 11B2 in a region around the boundary Ath2 between the first base end section 11B1 and the second base end section 11B2. According to one embodiment, the value of the rigidity Sb1 and the value of the rigidity Sb2 each may decrease linearly from the first base end section 11B1 to the second base end section 11B2 in the region around the boundary Ath2. A value of the rigidity Sa of the tip-flexible part 11A may gradually increase from the tip end of the catheter tube 11 to the base end of the catheter tube 11. According to one embodiment, the value of the rigidity Sa may increase linearly from the tip end to the base end of the catheter tube 11.

The rigidity Sa of the tip-flexible part 11A may be in a numerical range from about 0 (zero) MPa to about 100 MPa without limitation, and may preferably range from about 0 MPa to about 75 MPa according to a preferred but non-limiting embodiment. The rigidity Sb1 of the first base end section 11B1 may be in a numerical range from about 60 MPa to about 120 MPa without limitation, and may preferably range from about 75 MPa to about 115 MPa according to a preferred but non-limiting embodiment. The rigidity Sb2 of the second base end section 11B2 may be in a numerical range from about 45 MPa to about 80 MPa without limitation, and may preferably range from about 45 MPa to about 75 MPa according to a preferred but non-limiting embodiment. Note that an example of the numerical range of each of the rigidity Sa, the rigidity Sb1, and the rigidity Sb2, i.e., flexural modulus of each of the tip-flexible part 11A, the first base end section 11B1, and the second base end section 11B2, is based on experimental data that was obtained from a predetermined bending test.
[Workings and Effects]
[A. Basic Operation]

The catheter 1 may allow for measurement of information on the internal temperature of a hollow organ inside the body, such as the esophagus, of a patient when being used for a medical treatment of arrhythmia, etc., of the patient, e.g., when being used for surgical ablation of the left atrium. Examples of the ablation performed upon the medical treatment may include a high-temperature ablation, i.e., a method that performs heating, that uses a high frequency current and a low-temperature ablation, i.e., a method that performs cooling, that uses liquid nitrous oxide, liquid nitrogen, etc.

Figure 4:
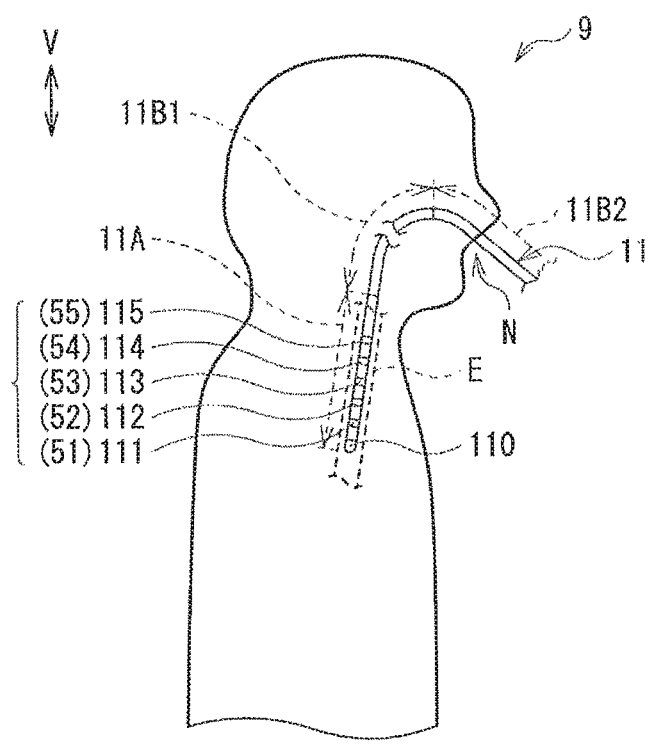
FIG. 4 schematically illustrates an example of how the catheter illustrated in FIG. 1 is used.

As schematically illustrated in FIG. 4, the catheter tube 11 of the catheter 1 is inserted from the tip end, i.e., from the tip-flexible part 11A, of the catheter tube 11 into the esophagus E of a patient 9 through, for example, the nose or the "nasal cavity N" of the patient 9 by means of a transnasal approach upon performing the measurement of the internal temperature. On this occasion, a shape near the tip end, i.e., the tip-flexible part 11A, of the inserted catheter tube 11 may be varied in two directions in response to the rotary operation of the rotary plate 41 performed by the operator of the catheter 1.

More specifically, for example, the operator may grab the handle 12 with his/her one hand and operate the knob 41a with its fingers to rotate the rotary plate 41 in a direction denoted by the arrow d1a of FIG. 1, i.e., in a clockwise direction. This pulls one of the foregoing pair of operating wires toward the base end within the catheter tube 11, thereby causing the region near the tip end of the catheter tube 11 to be curved or "deflected" in a direction denoted by the arrow d2a of FIG. 1.

Further, for example, the operator may operate the knob 41b to rotate the rotary plate 41 in a direction denoted by the arrow d1b of FIG. 1, i.e., in a counterclockwise direction. This pulls the other of the foregoing pair of operating wires toward the base end within the catheter tube 11, thereby causing the region near the tip end of the catheter tube 11 to be curved in a direction denoted by the arrow d2b of FIG. 1.

Performing the rotary operation of the rotary plate 41 by the operator in this way makes it possible to swing and deflect the tip-flexible part 11A of the catheter tube 11. Further, rotating the handle body 121 about an axis in an X-Y plane makes it possible to set an orientation of the tip-flexible part 11A freely in a direction of the deflection, i.e., in a curving direction, while the catheter tube 11 is inserted in the body, such as the esophagus E, of the patient 9. The catheter 1 may be thus provided with the deflection mechanism directed to the deflection of the tip-flexible part 11A, allowing for the insertion of the catheter tube 11 while varying a shape of the region near the tip end, i.e., the tip-flexible part 11A, of the catheter tube 11. Accordingly, it is possible to make the catheter tube 11 pass through the complex-structured nasal cavity N smoothly and insert the catheter tube 11 to the esophagus E easily. It is also possible to cause the tip-flexible part 11A to be pressed against a relevant part of the esophagus E while bringing the tip-flexible part 11A into close contact with the relevant part of the esophagus E.

The tip-flexible part 11A of the catheter tube 11 may include the five metal rings 111 to 115 serving as the temperature measuring metal rings. The tip-flexible part 11A also includes the five temperature sensors 51 to 55 electrically coupled to the metal rings 111 to 115 in an individual fashion, respectively. Utilizing those metals rings 111 to 115 and temperature sensors 51 to 55 allows for measurement or monitoring of the information on the internal temperature of the esophagus E. Note that the metal ring 111 and the metal ring 115 are so disposed as to respectively measure the lower side and the upper side of the esophagus when the catheter tube 11 is inserted, from the tip end of the catheter tube 11, into the esophagus E of the patient 9 as illustrated in FIG. 4. The lower side and the upper side may be, in other words, the stomach side and the oral cavity side, respectively.

By monitoring the internal temperature of the esophagus E of the patient 9 by means of the catheter 1, it is possible to avoid a possibility that the esophagus E is damaged upon, for example, the foregoing surgical ablation of the left atrium. More specifically, when performing ablation of a site such as the posterior wall of the left atrium of the heart by means of an ablation catheter, i.e., upon the surgical ablation of the left atrium, the esophagus located in the vicinity of the posterior wall of the left atrium may typically be heated or cooled as well, leading to a possible damage of the esophagus. Monitoring the internal temperature of the esophagus E in this way makes it possible to take a precaution and thus to avoid the possibility of the damage.

[B. Workings and Effects of Catheter Tube 11]

The catheter tube 11 of the catheter 1 according to the example embodiment has a configuration in which the first base end section 11B1 and the second base end section 11B2 are provided at the base end of the tip-flexible part 11A of the catheter tube 11, as illustrated by way of example in FIGS. 1 and 3. The first base end section 11B1 is disposed closer to the tip-flexible part 11A than the second base end section 11B2. The second base end section 11B2 is disposed at the base end of the first base end section 11B1, and has the rigidity lower than the rigidity of the first base end section 11B1.

The second base end section 11B2 located relatively on the base end side has the rigidity $Sb2$ that is lower than the rigidity $Sb1$ of the first base end section 11B1 ($Sb2<Sb1$). In other words, the second base end section 11B2 is softer than the first base end section 11B1. Thus, the catheter 1 according to the example embodiment makes it possible to reduce a burden imposed on the patient 9 with respect to the nasal cavity N or any other site, when the catheter tube 11 is inserted nasally from the tip-flexible part 11A into the hollow organ such as the esophagus E and placed inside the hollow organ.

More specifically, when the catheter tube 11 is inserted nasally from the tip-flexible part 11A into the esophagus E and placed inside the esophagus E, the second base end section 11B2 having the relatively low rigidity $Sb2$, i.e., $Sb2<Sb1$, is located around the nasal cavity N of the patient 9 as illustrated by way of example in FIG. 4. This reduces a possibility of damaging the inside or the medial wall of the nasal cavity N or any other site, and thus allows for the reduction in the burden imposed on the patient 9.

In contrast, in a catheter according to a comparative example where rigidity gradually increases from a tip end of a catheter tube to a base end of the catheter tube (i.e., $Sa<Sb1<Sb2$), the second base end section having the relatively high rigidity is located around the nasal cavity N of the patient 9 when the catheter tube is inserted into the esophagus E and placed inside the esophagus E. In other words, the relatively-hard second base end section is located around the nasal cavity N of the patient 9. Unlike the catheter 1 according to the example embodiment, this increases the possibility of damaging the inside of the nasal cavity N or any other site, which in turn increases the burden imposed on the patient 9.

In addition, in the catheter 1 according to the example embodiment, the rigidity $Sb2$ of the second base end section 11B2 may be substantially flat in value in the axial direction of the catheter tube 11, as illustrated by way of example in FIG. 3. This allows characteristics, such as the characteristics of the rigidity $Sb2$, of the second base end section 11B2 to be uniform in the axial direction, and allows for easier manufacturing of the catheter tube 11 accordingly.

Further, the rigidity $Sb1$ of the first base end section 11B1 may be higher than the rigidity $Sa$ of the tip-flexible part 11A ($Sb1>Sa$) in the catheter 1 according to the example embodiment, as illustrated by way of example in FIG. 3. This ensures flexibility of the tip-flexible part 11A, thereby facilitating the deflection operation and achieving good insertability into the entrance of the esophagus E.

Moreover, the catheter 1 according to the example embodiment may include the handle 12 that has the rotary operation part 122 as illustrated in FIG. 1. The rotary operation part 122 may allow the tip-flexible part 11A to perform the deflection operation. This allows for the insertion of the catheter tube 11 while varying the shape of the region near the tip end, i.e., the tip-flexible part 11A, of the catheter tube 11. Accordingly, for example, it is possible to make the catheter tube 11 pass through the complex-structured nasal cavity N smoothly and insert the catheter tube 11 to the esophagus E easily. It is also possible to cause the tip-flexible part 11A to be pressed against a relevant part of the esophagus E while bringing the tip-flexible part 11A into close contact with the relevant part of the esophagus E, for example.

The catheter 1 according to the foregoing example embodiment includes the base end part 11B provided at the base end of the tip-flexible part 11A of the catheter tube 11. The base end part 11B includes the first base end section 11B1 and the second base end section 11B2. Thus, it is possible to reduce the burden imposed on the patient 9 with respect to the nasal cavity N or any other site, when the catheter tube 11 is inserted nasally from the tip-flexible part 11A into the esophagus E and placed inside the esophagus E. Hence, it is possible to improve convenience upon use of the catheter 1.

MODIFICATION EXAMPLES

Although the technology has been described with reference to some example embodiments, the technology is not limited to such embodiments but may be modified in a wide variety of ways.

For example, shapes, locations, properties including the characteristics of the rigidity, materials, etc., of the respective members described in the foregoing example embodiments are non-limiting, and may respectively be any other shape, location, characteristic, material, etc.

In addition, although the catheter tube 11 has been described with specific reference to the configuration thereof in the foregoing example embodiments, it is not necessary for the catheter tube 11 to include all of the components.

Alternatively, the catheter tube 11 may be further provided with any other component. In one specific but non-limiting embodiment, the catheter tube 11 may include, as a swinging member, a plate spring provided inside the catheter tube 11 and deformable in a direction of flexure. Factors such as locations, shapes, and the number of metal rings 111 to 115 and the tip 110 of the catheter tube 11 are not limited to those referred to in the foregoing example embodiments as well. Further, the number of temperature sensors serving as the temperature measuring metal rings and the number of conduction wires are both not limited to those, i.e., five, described in the foregoing example embodiments, and may be adjusted in an example range from one to 20 on an as-needed basis. It is, however, preferable that the number of temperature sensors and the number of conduction wires both be 2 or more, preferably be about four or more, for the reasons described above. In addition, the foregoing example embodiments have been described by referring to an example in which no temperature sensor is electrically coupled to the tip 110; however, this is non-limiting and the temperature sensor may also be electrically coupled to the tip 110 to allow the tip 110 to have a function of measuring the temperature as well. Each of the temperature sensors, including the previously-mentioned sensor, is not limited to a configuration described in the foregoing example embodiments in which the thermocouple is used, and may utilize other sensors such as a thermistor. The metal rings 111 to 115 and the temperature sensors 51 and 55 do not necessarily have to be electrically coupled. The temperature sensors are not limited to those described in the foregoing example embodiments which are directed to measurement of the internal temperature of the hollow organ inside the body such as the esophagus, and may be those directed to measurement of a temperature of any other site. In other words, the temperature sensors may be so configured as to allow the catheter to function as a catheter directed to the measurement of the temperature of any other site.

Further, although the handle 12 including the handle body 121 and the rotary operation part 122 has been described with specific reference to the configuration thereof in the foregoing example embodiments, it is not necessary for the handle 12 to include all of the components. Alternatively, the handle 12 may be further provided with any other component. A configuration of the operation part of the handle 12 is not limited to the configuration based on the rotary operation part 122. Alternatively, the handle 12 may include the operation part having any other configuration.

In addition, a configuration of the shape near the tip end of the catheter tube 11 is not limited to that described in the forgoing example embodiments. Specifically, the forgoing example embodiments have been described with reference to an example of the catheter 1 that is of a type referred to as a "bidirectional type" in which the shape near the tip end, i.e., the tip-flexible part 11A, of the catheter tube 11 is varied in two directions in response to an operation made through the rotary plate 41. The technology, however, is not limited thereto. For example, the technology is applicable to a catheter of a type referred to as a "single direction type" in which the shape near the tip end of the catheter tube 11 is varied in one direction in response to an operation made through the rotary plate 41. In this case, only a piece of or a single operating wire may be provided as the previously-described operating wire.

Furthermore, the technology encompasses any possible combination of some or all of the various embodiments and the modifications described herein and incorporated herein.

Further, effects described herein are illustrative and non-limiting. Effects achieved by the technology may be those that are different from the above-described effects, or may include other effects in addition to those described above.

It is possible to achieve at least the following configurations from the above-described example embodiments of the disclosure.

(1) A catheter that measures an internal temperature of a hollow organ inside body, the catheter including:

a catheter tube including a tip-flexible part and a base end part, the tip-flexible part being configured to perform a deflection operation, the base end part being provided at a base end of the tip-flexible part; and one or a plurality of temperature sensors provided in the tip-flexible part, the base end part including a first base end section and a second base end section, the first base end section being provided closer to the tip-flexible part than the second base end section, and having rigidity that is higher than rigidity of the tip-flexible part, the second base end section being provided at a base end of the first base end section, and having rigidity that is lower than the rigidity of the first base end section, in which the tip-flexible part has a length in an axial direction of the tip-flexible part in a range from 40 mm to 100 mm, the first base end section has a length in an axial direction of the first base end section in a range from 200 mm to 400 mm, the second base end section has a length in an axial direction of the second base end section in a range from 200 mm to 900 mm, and a value of the rigidity of the first base end section and a value of the rigidity of the second base end section decrease linearly from the first base end section to the second base end section, in a region around a boundary between the first base end section and the second base end section.

The catheter according to an embodiment of the technology includes the first base end section and the second base end section that are provided at the base end of the tip-flexible part of the catheter tube. The first base end section is provided closer to the tip-flexible part than the second base end section, and has the rigidity that is higher than the rigidity of the tip-flexible part. The second base end section is provided at the base end of the first base end section, and has the rigidity that is lower than the rigidity of the first base end section. According to this embodiment, the second base end section located relatively on the base end side has the rigidity that is lower than the rigidity of the first base end section. For example, this reduces a burden imposed on a patient with respect to the nasal cavity or any other site, when the catheter tube is inserted nasally from the tip-flexible part into the hollow organ and placed inside the hollow organ. Further, according to this embodiment, the rigidity of the first base end section is higher than the rigidity of the tip-flexible part. This ensures flexibility of the tip-flexible part, thereby facilitating the deflection operation and achieving good insertability into an entrance of the hollow organ.

In addition, in the region around the boundary between the first base end section and the second base end section, the value of the rigidity of the first base end section and the value of the rigidity of the second base end section decrease linearly from the first base end section to the second base end section. This improves the insertability of the catheter tube into the body. This also makes it difficult for the catheter tube or a catheter shaft to cause kink, or desirably makes it possible to prevent the occurrence of kink of the catheter tube or the catheter shaft.

(2) The catheter according to (1), in which the value of the rigidity of the second base end section is substantially flat in an axial direction of the catheter tube.

This allows characteristics, such as the characteristics of the rigidity, of the second base end section to be uniform in the axial direction, and allows for easier manufacturing of the catheter tube accordingly.

(3) The catheter according to (1) or (2), in which a value of the rigidity of the tip-flexible part increases linearly from a tip end of the catheter tube to the first base end section.

(4) The catheter according to any one of (1) to (3), further including a handle that includes an operation part, the operation part allowing the tip-flexible part to perform the deflection operation.

This allows for insertion of the catheter tube while varying a shape of a region near the tip end, i.e., the tip-flexible part, of the catheter tube. Accordingly, for example, it is possible to make the catheter tube pass through the complex-structured nasal cavity smoothly and insert the catheter tube to the hollow organ easily.

(5) The catheter according to any one of (1) to (4), in which the hollow organ includes esophagus.

This allows the tip-flexible part to be pressed against a relevant part of the esophagus while bringing the tip-flexible part into close contact with the relevant part of the esophagus.

(6) The catheter according to (5), in which the second base end section is located around nasal cavity when the catheter tube is inserted nasally from the tip-flexible part into the esophagus and placed inside the esophagus.

This reduces a possibility of damaging inside or medial wall of the nasal cavity or any other site, and thus allows for the reduction in the burden imposed on the patient.

The catheter according to the above-described embodiment includes the base end part provided at the base end of the tip-flexible part of the catheter tube. The base end part includes the first base end section and the second base end section. Thus, it is possible to reduce the burden imposed on the patient with respect to the nasal cavity or any other site, when the catheter tube is inserted nasally from the tip-flexible part into the hollow organ and placed inside the hollow organ. Hence, it is possible to improve convenience upon use of the catheter.

Although the technology has been described in terms of exemplary embodiments, it is not limited thereto. It should be appreciated that variations may be made in the described embodiments by persons skilled in the art without departing from the scope of the technology as defined by the following claims. The limitations in the claims are to be interpreted broadly based on the language employed in the claims and not limited to examples described in this specification or during the prosecution of the application, and the examples are to be construed as non-exclusive. For example, in this disclosure, the term "preferably", "desirably" or the like is non-exclusive and means "preferably", but not limited to.

The use of the terms first, second, etc. do not denote any order or importance, but rather the terms first, second, etc. are used to distinguish one element from another. Moreover, no element or component in this disclosure is intended to be dedicated to the public regardless of whether the element or component is explicitly recited in the following claims.

What is claimed is:

1. A catheter that measures an internal temperature of a hollow organ inside a body, the catheter comprising:
   a catheter tube including a tip-flexible part and a base end part, the tip-flexible part being configured to perform a deflection operation, the base end part being provided at a base end of the tip-flexible part; and
   one or a plurality of temperature sensors provided in the tip-flexible part,
   the base end part including a first base end section and a second base end section,
       the first base end section being provided closer to the tip-flexible part than the second base end section, and having rigidity that is higher than rigidity of the tip-flexible part,
       the second base end section being provided at a base end of the first base end section, and having rigidity that is lower than the rigidity of the first base end section, wherein
   the tip-flexible part has a length in an axial direction of the tip-flexible part in a range from 40 mm to 100 mm,
   the first base end section has a length in an axial direction of the first base end section in a range from 200 mm to 400 mm,
   the second base end section has a length in an axial direction of the second base end section in a range from 200 mm to 900 mm, and
   a value of the rigidity of the first base end section and a value of the rigidity of the second base end section decrease linearly from the first base end section to the second base end section, in a region around a boundary between the first base end section and the second base end section.

2. The catheter according to claim 1, wherein the value of the rigidity of the second base end section is substantially flat in an axial direction of the catheter tube.

3. The catheter according to claim 1, wherein a value of the rigidity of the tip-flexible part increases linearly from a tip end of the catheter tube to the first base end section.

4. The catheter according to claim 1, further comprising a handle that includes an operation part, the operation part allowing the tip-flexible part to perform the deflection operation.

5. The catheter according to claim 1, wherein the hollow organ comprises esophagus.

6. The catheter according to claim 5, wherein the second base end section is located around nasal cavity when the catheter tube is inserted nasally from the tip-flexible part into the esophagus and placed inside the esophagus.

* * * * *